United States Patent [19]
Radcliffe et al.

[11] Patent Number: 5,942,700
[45] Date of Patent: Aug. 24, 1999

[54] SYSTEMS AND METHODS FOR COLLECTING FLUID SAMPLES HAVING SELECT CONCENTRATIONS OF PARTICLES

[75] Inventors: Gail E. Radcliffe, Worcester; Daniel C. Lapen, Lancaster; Charles A. Festel, Newton, all of Mass.

[73] Assignee: Cytyc Corporation, Boxborough, Mass.

[21] Appl. No.: 08/742,647

[22] Filed: Nov. 1, 1996

[51] Int. Cl.⁶ .................................................. G01N 1/20
[52] U.S. Cl. ................................... 73/863.24; 73/863.02
[58] Field of Search .......................... 73/863.23, 863.24, 73/863.25, 863.01, 863.02, 863.03, 61.73

[56] References Cited

U.S. PATENT DOCUMENTS

| | | | |
|---|---|---|---|
| 164,451 | 6/1875 | Hellen | 73/863.23 X |
| 3,452,586 | 7/1969 | Childs et al. | 73/61.73 |
| 3,495,463 | 2/1970 | Howell | 73/863.24 X |
| 4,446,725 | 5/1984 | Schulz, Jr. | 73/863.24 X |
| 4,727,758 | 3/1988 | Murdock | 73/863.24 X |
| 5,095,740 | 3/1992 | Hodgson et al. | 73/61.73 |
| 5,190,666 | 3/1993 | Bisconte | 210/744 |
| 5,308,483 | 5/1994 | Sklar et al. | 73/863.23 X |
| 5,375,477 | 12/1994 | Neill et al. | 73/863.23 |
| 5,624,815 | 4/1997 | Grant et al. | 73/863.23 X |

FOREIGN PATENT DOCUMENTS

| | | |
|---|---|---|
| 2 643 285 | 8/1990 | France . |
| 2 672 995 | 8/1992 | France . |
| 32 23 589 | 12/1983 | Germany . |
| 917035 | 4/1982 | U.S.S.R. ............ 73/863.23 |
| 1160265 | 6/1985 | U.S.S.R. ............ 73/863.24 |
| WO 95/14533 | 6/1995 | WIPO . |
| WO 96/14578 | 5/1996 | WIPO . |

OTHER PUBLICATIONS

Patent Abstracts of Europe (DE 03223589 A1) Dec. 29, 1983 Aekins.
Patent Abstracts of Europe (WO 09010211A1) Sep. 7, 1990 Hoegaerden et al. "Process and Device for Filtering Liquid or Gas Samples Laden with Particles to be Analyzed".
Patent Abstracts of Europe (FR 0262995A) Aug. 21, 1992 Patrick et al.

*Primary Examiner*—Thomas P. Noland
*Attorney, Agent, or Firm*—Testa, Hurwitz & Thibeault, LLP

[57] ABSTRACT

Instruments and processes according to the invention provide for the preparation of a fluid sample that has a substantially known concentration of a select particulate matter. In one aspect, the invention is understood as laboratory instruments for sample preparation. These instruments can include a filter that is submersible within a fluid suspension of particulate matter. To collect particulate matter from the fluid suspension, the instruments can cause a fluid flow that pulls fluid across the filter to trap particulate matter against one surface of the filter. The instruments can then remove the filter from the fluid suspension and dispose the filter above a collection vessel such that the side of the filter that is carrying particulate matter is positioned above the opening of the collection vessel. The laboratory instruments can then send a collection fluid through the filter in a direction opposite to the original fluid flow, thereby washing the particulate matter off the filter and into the collection vessel. The laboratory instruments according to the invention can provide samples having a known concentration by passing a known volume of collection fluid through the filter, thereby trapping the collected particulate matter within a known volume of collection fluid.

15 Claims, 5 Drawing Sheets

SYSTEMS AND METHODS FOR COLLECTING FLUID SAMPLES HAVING SELECT CONCENTRATIONS OF PARTICLES

FIELD OF THE INVENTION

The invention generally relates to laboratory instruments and processes for collecting samples and, more particularly, to laboratory instruments and processes to generate fluid samples that have known concentrations of a targeted particulate material.

BACKGROUND OF THE INVENTION

In chemistry and the biological sciences, laboratory instruments and techniques exist for separating a composite material, such as a soil sample or a blood sample, into its component materials. Typically, the isolation step is performed as a preliminary step to further testing that centers around the characteristics of the isolated component.

It is often a difficult and cumbersome task to isolate one element of a composite material. One typical approach is to employ a centrifuge to separate composite materials into the individual elements. In practice, a lab technician can place the composite material into a test-tube-like container. The lab technician inserts the container into the centrifuge and activates the centrifuge for sufficient time to separate out the element or elements of interest. Upon completion of a centrifugal separation, the lab technician removes the container and extracts from the stratified sample the element or elements.

Although centrifugal separation can work well, it is typically labor-intensive and often poorly suited for isolating small particulate matter, such as cellular material. Moreover, the centrifugal technique fails to provide a separation process that readily yields samples with known concentrations of a targeted element.

Accordingly, it is an object of the invention to provide laboratory instrumentation and processes that generate samples with known concentrations of a selected particulate material.

It is a further object of the invention to provide laboratory instruments and processes that detect samples having low concentrations of a targeted material.

It is yet a further object of the invention to provide laboratory instrumentation and processes that provide measures of the integrity of a performed diagnostic analysis.

It is still a further object of the invention to provide instrumentation and techniques that provide information representative of the severity of a disease.

Other objects of the invention will in part be obvious and will in part appear hereinafter.

SUMMARY OF THE INVENTION

Instruments and processes according to the invention provide for the preparation of a fluid sample that has a substantially known concentration of a select particulate matter. In one aspect, the invention is understood as laboratory instruments for sample preparation. These instruments can include a filter that is submersible within a fluid suspension of particulate matter. To collect particulate matter from the fluid suspension, the instruments can cause a fluid flow that pulls fluid across the filter to trap particulate matter against one surface of the filter. The instruments can then remove the filter from the fluid suspension and dispose the filter above a collection vessel such that the side of the filter that is carrying particulate matter is positioned above the opening of the collection vessel. The laboratory instruments can then send a collection fluid through the filter in a direction opposite to the original fluid flow, thereby washing the particulate matter off the filter and into the collection vessel. The laboratory instruments according to the invention can provide samples having a known concentration by passing a known volume of collection fluid through the filter, thereby trapping the collected particulate matter within a known volume of collection fluid.

In one aspect, the invention is understood as methods for reproducibly generating a fluid sample having a select concentration of particles. Methods of the invention can include the steps of providing a fluid suspension of dispersed particles, disposing a filter having a first side and a second side within the fluid suspension and flowing the fluid suspension across the filter from the first side to the second side, such that a substantially known quantity of particles collect onto the first side of the filter, removing the filter and the particles collected thereon from the fluid suspension, and passing a known volume of collection fluid through the filter to remove substantially the particles collected on the first side, and to collect the particles within the known volume of collection fluid.

In one practice, the processes according to the invention can include a step of disposing a filter that includes providing a particle collection device having an intake port and an evacuation port, and having the filter spanning the intake port. Further practices according to the invention can include a step of generating a fluid flow by evacuating the particle collection device to draw fluid across the filter and through the intake port and into the collection device.

In a further practice of the invention, these processes can include a step of passing a known quantity of collection fluid through the filter by applying a select fluid pressure within the collection device to force fluid collected therein back across the filter. Further, when passing a known volume of collection fluid through the filter, the processes of the invention can include the step of disposing the filter collection device at a select angle to generate thereby a drip of collection fluid that has the particles collected therein.

In a further practice, the invention can include the steps of selecting a filter that has a pore size adapted, dimensionally, for collecting particles of a predetermined size. These filters can include cellulose, polyester, polycarbonate, nylon and teflon filters, and can have pore sizes suited for collecting a target material. For cells, filter pore sizes typically range between 0.2 and 20 microns.

The processes according to the invention can also include further steps for analyzing the particles and fluid samples that are collected. For example, the processes of the invention can include the further steps of lysing the collected particles, or providing a portion of the collected particles in the known volume of collection fluid as a sample for diagnostic assay.

In a further practice, the processes according to the invention can include the steps of causing a flow of fluid and measuring a characteristic representative of the quantity of particles collected against the filter. Moreover, the processes can interrupt the step of flowing the fluid suspension in response to a measured characteristic that represents a preselected quantity of particles. Accordingly, processes according to the invention can monitor characteristics of the fluid flow to determine when a preselected quantity of particles have collected against the filter.

In a further aspect, processes according to the invention can direct the fluid suspension across the filter by applying a known pressure to the fluid suspension. Further these processes can apply pressure to the fluid suspension as a succession of know pressures. In this practice, the processes can measure a characteristic representative of the rate of change of pressure and can determine from this measured characteristic a quantity of particles collected against the filter surface.

In a further aspect, the invention provides processes that can be employed for incrementally achieving a desired concentration of particles within a known volume of fluid. For example, the processes of the invention can be iterative in that upon collecting a first sample of collected particles within a known volume of fluid, this fluid sample can be again processed according to the invention to provide a fluid sample having an alternative concentration of particles.

In a further aspect, the invention provides apparatus for reproducibly collecting a sample having a select concentration. Such apparatus can comprise a filter having a first side and a second side and being submersible within a fluid that contains a quantity of particles, an element for flowing the fluid across the filter in a direction that travels from the first side to the second side such that a substantially known quantity of particles collects onto the first side of the filter, an element for removing the filter and the particles collected thereon from the fluid suspension, and an element for passing a known volume of collection fluid through the filter to remove substantially the particles collected on the first side and to collect the particles within a known volume of collection fluid.

As described above, the invention offers significant advantages over known methods for collecting fluid samples by providing systems and methods that generate fluid samples of particulate material in select concentrations. Moreover, the invention further provides automated laboratory instrumentation that can perform each step of the fluid sample preparation process such that the systems automatically and reproducibly provide fluid samples each having select and known concentrations.

These and other advantages of the invention will be more fully understood by reference to the following detailed description in conjunction with the accompanying drawings in which like reference numbers refer to like elements.

BRIEF DESCRIPTION OF ILLUSTRATED EMBODIMENTS

Figure 1:
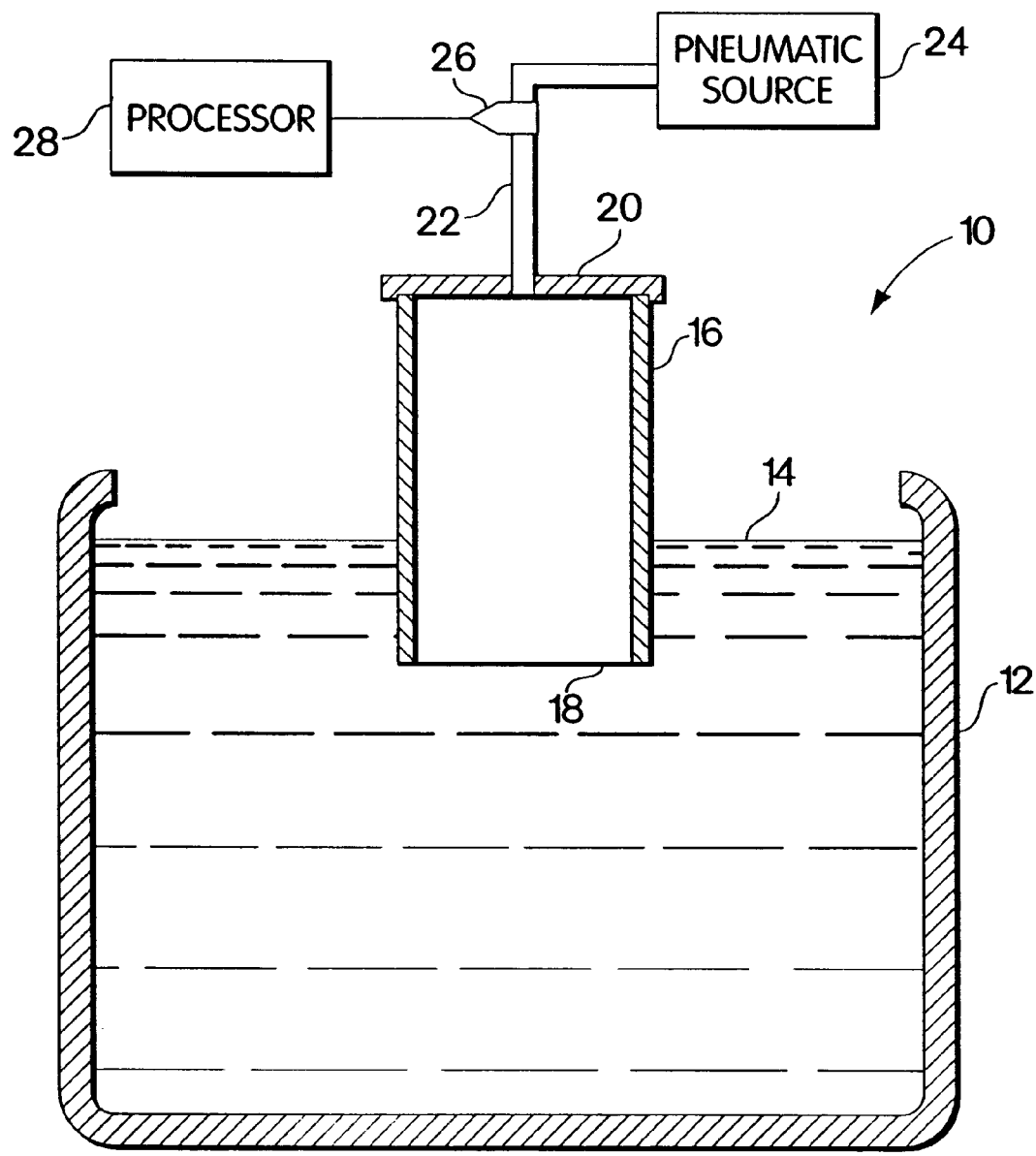
FIG. 1 illustrates in functional block diagram form one system according to the invention for providing a fluid sample having a select concentration.
Figure 5A:
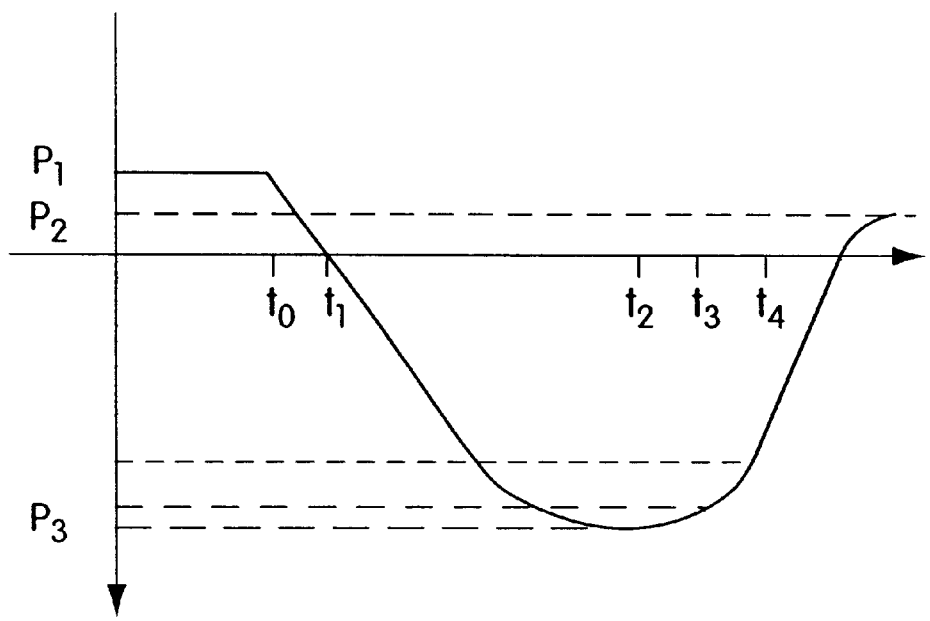
Figure 5B:
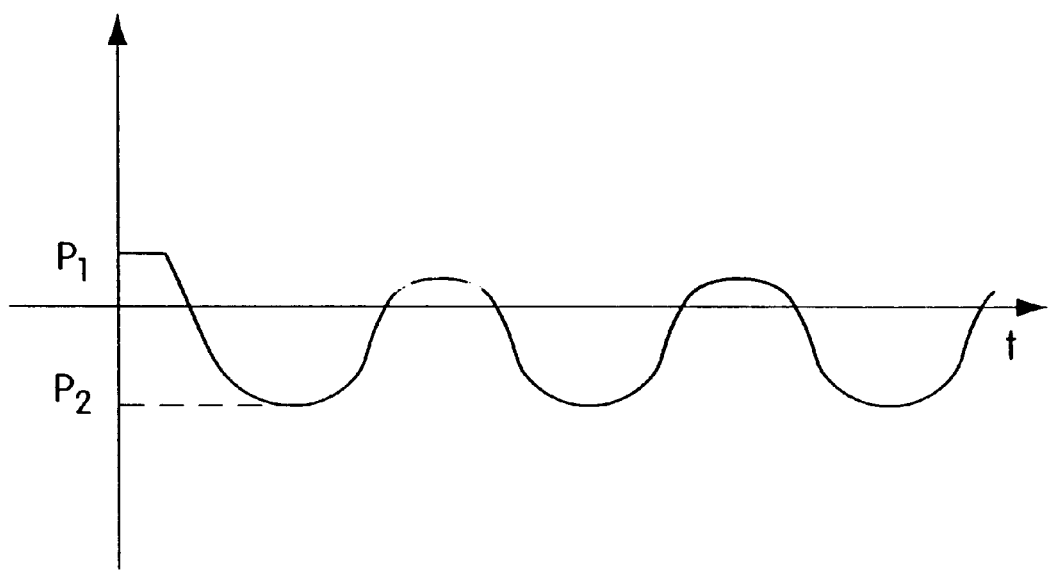

FIGS. 5a and 5b diagramatically illustrate known pressures suitable for drawing fluid across the filter depicted in FIG. 1.

Figure 6:
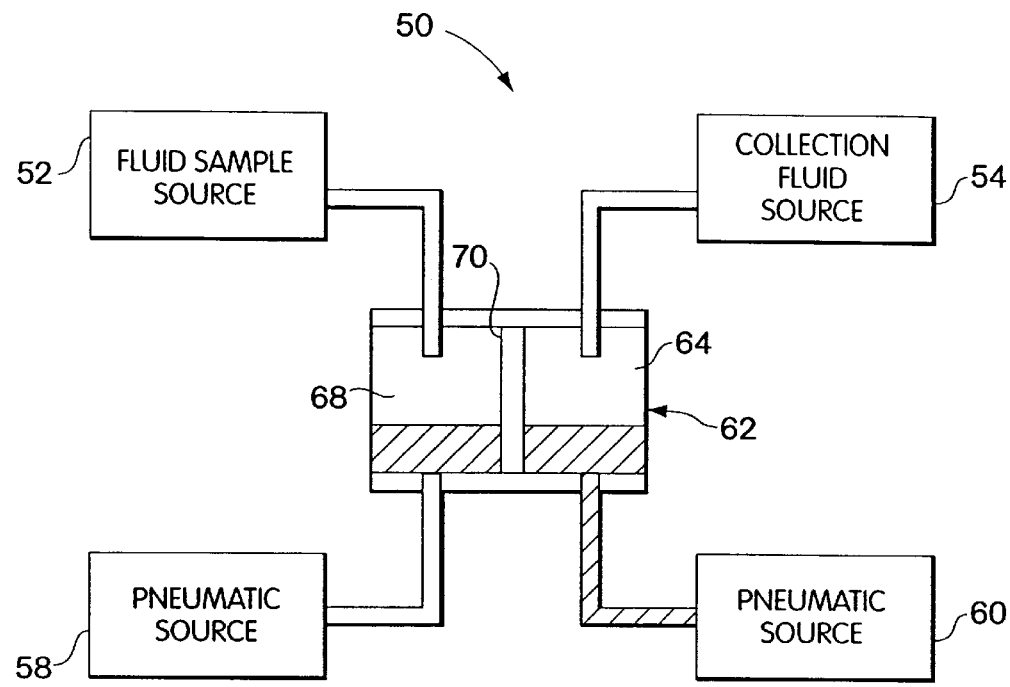
Figure 7:
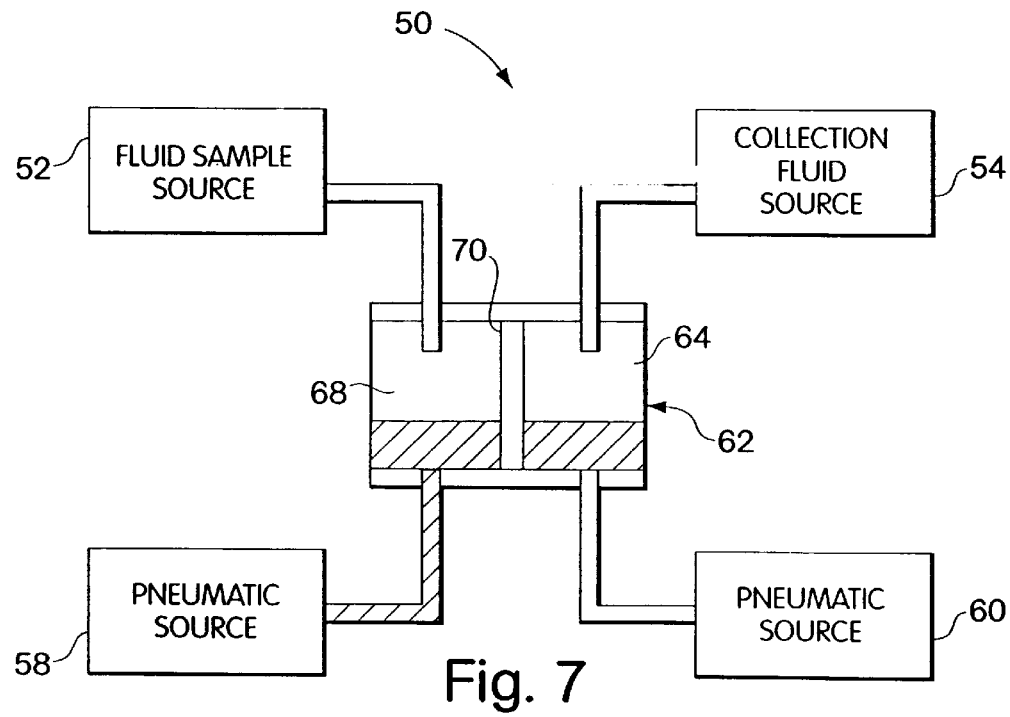

FIGS. 6 and 7 illustrate an alternative embodiment of the invention.

DETAILED DESCRIPTION OF THE ILLUSTRATED EMBODIMENTS

FIG. 1 depicts the functional elements of one embodiment of the invention. More particularly, FIG. 1 depicts a system 10 that includes a container 12, a fluid suspension of dispersed particles 14, a particle collection device 16, a filter 18, a cap 20, a conduit 22, a pneumatic source 24, and a processor 28.

The container 12 holds the fluid sample 14, and makes it available for sampling by the collection device 16. In the illustrated embodiment, the system 10 uses a pneumatic particle collection technique wherein the system 10 employs pneumatic action provided by the pneumatic source 24 to draw a portion of the fluid sample 14 past the filter 18 and into the collection device 16. Particles dispersed within the fluid sample 14 collect onto one side of the filter 18 and can be removed from the fluid sample 14 by extraction of the particle collection device 16. During collection of the particles against filter 18, the processor 28 determines a measure representative of the quantity of particles that have collected against the filter 18. Accordingly, upon extraction of the collection device 16 from the sample 14, the system 10 has collected a substantially known quantity of particles from the fluid sample 14.

The container 12 can be any container suitable for holding a fluid material and for providing access to the fluid material by a particle collection device, such as the device 16. When practicing the invention with a fluid sample having biological particles dispersed therein, the container 12 is commonly a sterilized plastic container suited for holding a biological sample and for disposal after the fluid sample 14 is processed by the system 10.

The fluid sample 14 depicted in FIG. 1 is a liquid sample that has dispersed therein a quantity of particles. Typically, the quantity of particles is relatively unknown and, therefore, the concentration of particles within the sample volume is also unknown. The particles within a fluid sample 14 are dispersed such that there exists, within the sample, some population of particles that are separate from, and independent of, any of the other particles. These disperse independent particles are well-suited for collection by the filter 18 as a portion of the fluid sample 14 is drawn across the filter 18 and into the collection device 16. Accordingly, in one practice of the invention, the system 10 disperses cells within the fluid sample 14 by actuating the particle to collection device 16. In one embodiment, the system 10 rapidly rotates the particle collection device 16 to actuate the fluid sample 14 and break-up clumps of particles that may exist within the fluid sample. For example, with a fluid sample 14 having contained therein a population of epithelial cells, the actuation of the collection device 16 can break-up clumped cells, such that there exists within the fluid sample 14 a population of individual cells, and a reduced population of clumped cells.

In one embodiment, the system 10 collects a known quantity of cells from a biological fluid sample 14. For example, the fluid sample 14 can be comprised of an aqueous preservation solution that contains a biological sample, such as tissue cells, blood cells, scrapings, aspirates, or other such biological materials and samples.

The particle collection device 16 depicted in FIG. 1 has a cylindrical sidewall, which is shown in cross section, that provides a rim for supporting the filter 18 that attaches at one end of device 16. At the opposite end of the filter 18, a cap 20 spans across the device 16 to fluidically seal the interior chamber of device 16. The cap 20 has an aperture that receives the fluid conduit 22 that fluidically couples the interior of device 16 with the pneumatic source 24. The sidewall of the particle collection device 16 can be a plastic material, such as polystyrene, that provides at one end, a rim suitable for attaching the filter 18. The filter 18 can be a polycarbonate membrane having a porosity selected for collecting particles of a particular size from the fluid sample 14. One such filter 18 is a polycarbonate membrane marketed by the Nuclepore Corporation in Pleasanton, Calif. Other filters can be formed from materials including cellulose, nylon, polyester, teflon, or any other suitable material. The filter membrane can have a pore size or sizes suitable for collecting cells of particular sizes and can be, for example, pores of size approximately 0.2 to 20 microns. Further, the depicted particle collection device 16 can be a filter cylinder device manufactured and marketed by the Cytyc Corporation of Boxboro, Mass., the assignee hereof. However, the pore size is to be selected as a function of the target material being collected.

FIG. 1 includes pneumatic system for evacuating fluid, typically air, from the interior of the device to draw a portion of the fluid sample 14 across the filter 18. The pneumatic system includes the source 24 and the conduit 22. As depicted in FIG. 1, the conduit 22 extends through the aperture of the cap 20 and replaces the interior of the particle collection device 16 in fluid communication with the pneumatic source 24. The pneumatic source 24 can be a vacuum source that evacuates the interior of the particle collection device 16, thereby creating a pressure differential across the filter 18, causing a portion of the fluid sample to cross the filter 18. The pneumatic source 24 can be any pneumatic source suitable for evacuating, or partially evacuating, the interior of the particle device 16 and thereby creating a pressure differential across the filter 18 that acts as negative pressure on the fluid sample 14.

As further shown in FIG. 1, the system 10 includes a sensor 26 that couples to the conduit 22 and that couples, via a transmission path, to the processor 28. In one embodiment of the invention, the sensor 26 is a pressure sensor that measures the pressure being applied by the pneumatic source 24 to the interior of the collection device 16. The sensor 26 acts as a transducer to generate an electrical signal representative of this pressure. The processor 28 receives the signal generated by the transducer sensor 26 and generates, responsive to this signal, a quantity signal representative of the quantity of particles that have collected against the surface of the filter 18. The sensor 26, in this embodiment of the invention, can be any sensor suitable for generating a signal representative of the pressure within the interior of the particle collection device 16. The processor 28 depicted in FIG. 1 can be any data processing system having an input interface for receiving a signal generated by a sensor element and capable of processing that signal to generate a quantity signal representative substantially of the number of particles that have collected against the filter 18.

Figure 2:
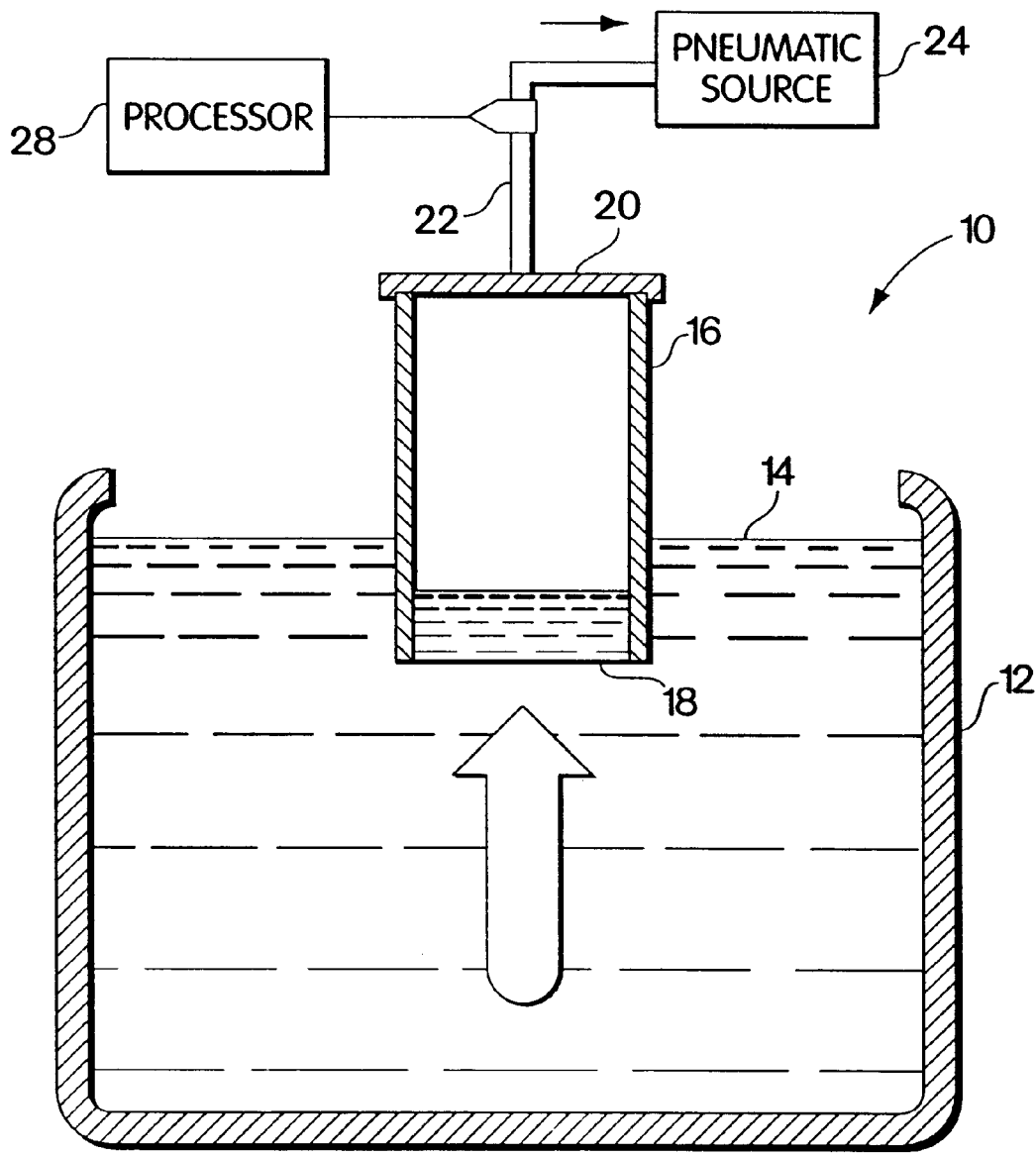
FIG. 2 illustrates the system of FIG. 1 in operation for collecting cells from a fluid suspension.

FIG. 2 depicts the system of FIG. 1 having drawn a portion of the sample fluid 14 across the filter 18 and into the interior of the collection device 16. As depicted in FIG. 2, the pneumatic source 24 creates a negative pressure within the interior of the collection device 16 that generates a flow of the fluid sample 14 across the filter 18. Drawing a fluid sample 14 across the filter 18 causes the particles dispersed within the fluid sample 14 to collect against the filter 18 and, in particular, to block the pores of the filter membrane.

The action of blocking the pores of the filter membrane 18 is understood to decrease effectively the porosity of the filter membrane. The amount of time it takes for the negative pressure to return to equilibrium after the pneumatic source has changed the interior pressure within the collection device 16 is dependent, in part, on the number of pores of filter 18 available for passing fluid into the interior of the device 16. Consequently, as particles collect against the filter surface 18, the pores of the filter 18 are sealed, thereby reducing the number of pores available for passing fluid to the interior of the device 16. The reduction of available pores can increase the amount of time it takes for the vacuum inside the collection device to return to equilibrium. Further, the rate of pressure change within device 16 changes as pores are blocked. Accordingly, the pressure change and rate of pressure change within the device 16 can be representative of the number of particles that have collected against the surface of the filter 18. Accordingly, the processor 28 can track the pressure within device 16 and determine, responsive thereto, a number representative of a quantity of particles collected against the filter 18.

In one embodiment of the invention, the system 10 creates a flow of fluid to the filter 18 until the processor 28 determines, from measures of the pressure within the device 16, that substantially each pore of filter 28 is blocked by a collected particle. For each filter 18, the number of pores is approximately known. Therefore, the processor 28 can generate a quantity signal representative of substantially the number of particles it takes to block each pore of the filter 18.

Alternatively, the processor 28 can determine from measures of the rate of pressure change within the device 16, quantity signals representative of the number of particles that have collected against the filter 18 to partially block the filter. Accordingly, in this embodiment, the system 10 can collect a known quantity of particles from a fluid sample 14 that has a population of particles dispersed therein which would be insufficient to completely obstruct the flow of fluid to the interior of the device 16.

The system 10 depicted in FIGS. 1 and 2 can be employed to determine the concentration of the dispersed particles within the fluid sample 14. In one practice, the system 10 draws a known volume of fluid across the filter 18. With a fluid sample 14 that has a uniformly, or substantially uniformly, dispersed particle population, the system 10 can determine the concentration of the fluid sample 14 responsive to the quantity of particles collected out of the known volume of fluid drawn across the filter 18. To this end, the pneumatic source 24 can draw a portion of the fluid sample 14 to the filter 18 and into the cylinder 16. The processor 28 can employ this known volume and a measure of the particles collected against filter 18 to measure the concentration of the fluid sample 14.

Figure 3:
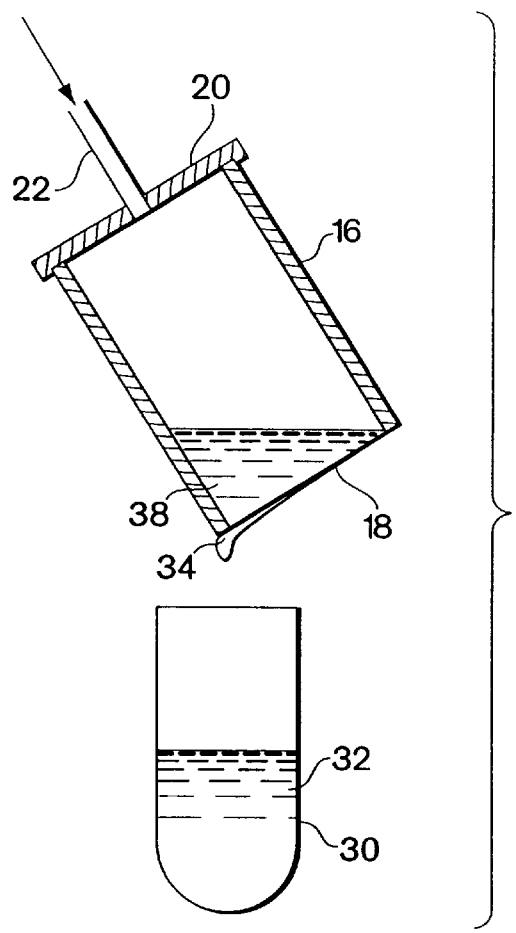
FIG. 3 illustrates the system of FIG. 1 in operation for collecting particles within a known volume of collection fluid.

In a further practice of the invention, the entire volume of the fluid sample 14 can be flowed across the filter 18 to collect and count the particles within the fluid suspension. In this practice, the system 10 can continuously filter a portion of the fluid sample 14 until the entire fluid sample 14 has been substantially processed by the system 10. Optionally, a plurality of filters can be sequentially disposed within the sample 14, employing a new filter each time a portion of the fluid sample 14 is processed. Alternatively, a process according to the invention can include a further step of rinsing the filter membrane after each time the filter processes a portion of the fluid sample 14. The rinsing process can include a step of disposing the filter 18 within a fluid bath and actuating the filter therein to remove particles collected against the membrane. Further, the step of rinsing the filter 18 can include the step of placing the filter 18 within a fluid bath and applying a positive pressure to the interior of the device 16 to effectively blow any particles collected onto the membrane into the cleansing fluid. Alternative practices for removing particles collected against the filter can be practiced with the invention without departing from the scope thereof FIG. 3 depicts a further step of the invention and shows the particle collection device 16 disposed above a collection 30 having a preservation fluid 32 contained therein. As depicted in FIG. 3, the collection device 16 is held at an angle such that a corner portion of a device 16 is disposed directly above the container 30 and the filter 18 is disposed at an angle relative to an axis extending parallel to the sides of the container 30. In this step, a known volume of collection fluid is passed through the filter 18 to remove substantially all the particles collected onto the opposite side of the filter 18 and to collect those particles within the known volume of collection fluid.

The collection fluid 38 depicted in FIG. 3 can be, in one practice, the filtrate generated by passing the fluid sample 14 through the filter 18. Alternatively, the collection fluid can be a preservation fluid passed into the interior of the particle collection device 16. In one practice of the invention, the pneumatic source 24 applies, via conduit 22, a positive pressure within the interior of the collection device 16 to effectively press a portion of the collection fluid 38 through the filter 18 thereby removing the particles from the surface of the filter 18, and collecting the particles within the fluid 38. As depicted in FIG. 3, a positive pressure is applied to the interior of the particle collection device 16 to pass a volume of collection fluid through the filter 18 to form a drop 34 of collection fluid having gathered therein substantially all the particles previously collected by the filter 18. As further illustrated in FIG. 3, the drop of collection fluid 34 can, with the particles contained therein, pass to the container 30. The process provides a known volume of preservation fluid 32 within the container 30. Accordingly, the process provides a fluid sample having a substantially known quantity of particles contained within a substantially known volume of fluid.

Figure 4A:
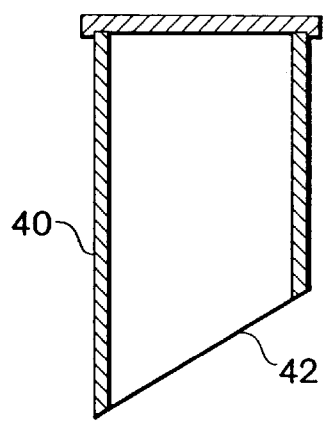
FIGS. 4a and 4b illustrate alternative embodiments of collection vessels suitable for practice with the system depicted in FIG. 1.
Figure 4B:
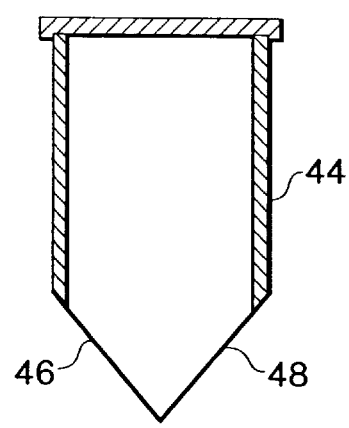

FIGS. 4a and 4b depict alternative embodiments of the collection devices suitable for practice with the present invention. In particular, FIG. 4a depicts a collection device 40 that has an edge 42 that extends transverse relative to the sidewalls of the collection device 40. This adjacent edge 42 facilitates the development of a drop of collection fluid having particles dissolved therein. Similarly, FIG. 4b depicts a further alternative embodiment of the collection device suitable for practice with the invention. The collection device 44 has a first edge 46 and a second edge 48, both which extend transverse to the sidewalls of the collection device 44. The opposing transverse edges 46 and 48 together facilitate the development of a drop of fluid. In each of the depicted particle collection devices, it will be understood that the filter can span entirely across one end of the collection device or can span across a portion of that collection device. It will further be understood that other particle collection devices can be practiced with the present invention without departing from the scope thereof.

FIGS. 5a and 5b depict pressure pulses suitable for drawing fluid across the filter 18. FIG. 5a depicts a first set of axes including a vertical axis labeled P designating the interior pressure of the collection device 16. FIG. 5a shows increasing pressure as values increase from $P_2$ to $P_1$. FIG. 5a also shows a horizontal axis, labeled T. The horizontal axis shows increasing time in the direction from $t_0$ to $t_1$. As shown in FIG. 5a, the pneumatic source 24 can act as a vacuum to decrease pressure within the device 16 from an initial pressure of $P_1$ to a subsequent pressure $P_2$. Pressure within the device decreases from $P_1$ to $P_3$ during the time interval between $t_0$ and $t_2$. As fluid enters the interior of the device, the pressure begins to equilibrate and particles collect against the filter surface. In one practice of the invention, the processor 28 measures the interior pressure and determines the time interval over which the interior pressure increases from $P_{90}$ to $P_{60}$, where $P_{90}$ represents an interior pressure that is approximately 90% of the peak negative pressure $P_3$ and $P_{60}$ represents an interior pressure that is approximately 60% of the peak negative pressure $P_3$. FIG. 5a depicts this time interval as occurring between $t_3$ and $t_4$. The processor 28 employs these time and pressure measurements to determine a rate of pressure change which is representative of the number of collected particles. This can include the processor 28 determining an exponential rate of decay of the interior pressure. As described above, the processor 28 can determine a quantity signal, responsive to the rate of pressure change within the device 16, and being representative of the number of particles collected against the filter 18.

FIG. 5b depicts an alternative practice of the invention wherein a plurality of pressure pulses is provided to the interior of the particle collection device 16. In this practice of the invention, the pneumatic source 24 employs several pressure pulses to draw a portion of the fluid sample 14 to the filter 18. The plural pulses are generally provided as a sequence of negative pressure bursts that act like a sequence of sips. The processor 28 can determine, each time the pneumatic source applies the negative pressure, the rate of pressure change within the collection device 16. This allows the processor 28 to monitor the quantity of particles collected against the filter 18. In one practice, upon detection of sufficient number of particles collected against the filter 18, the system 10 removes the filter 18 from the fluid sample and, as described with reference to FIG. 3, collects the selected quantity of particles within a known volume of collection fluid.

FIGS. 6 and 7 depict a further alternative embodiment of the invention. More particularly, FIG. 6 depicts a system 50 that includes a fluid sample source 52, a collection fluid source 54, a pneumatic source 58, a pneumatic source 60, a collection device 62, having a first chamber 64 and a second chamber 68, and a filter 70 disposed between the chambers 64 and 68. The fluid sample source 52 can contain a fluid sample of dispersed particles. Fluid sample source 52 can provide the fluid suspension of dispersed particles into the container 62 via the fluid conduit that couples between sample source 52 and the container section 68. The pneumatic source 60 can apply a negative pressure within the interior of the container chamber 64 to draw a portion of the fluid sample across the filter 70. In the depicted embodiment, the pneumatic source 60 evacuates the chamber 64 of all filtrate leaving chamber 64 empty. The system 50 can then activate collection source 54 to provide collection fluid into the chamber 64 of particle collection device 62. The pneumatic source 58 can draw collection fluid across the filter 70 to collect, within the collection fluid, the quantity of particles collected against the filter 70. The pneumatic source 58 can draw selected amounts of the collection fluid past filter 70 to collect the particles within a known volume of collection fluid.

It will thus be seen that the invention efficiently attains the objects set forth above, among those made apparent from the preceding description. Since certain charges may be made in the above instrument and process without departing from the scope of the invention, it is intended that all matter containing the above description or shown in the accompanying drawings be interpreted as illustrative and not in a limiting sense.

It is also to be understood that the following claims are intended to cover all generic and specific features of the invention herein described, and all statements of the scope of the invention which, as a matter of language, might be said to fall therebetween.

What is claimed is:

1. A method for collecting a fluid sample having a select concentration of particles, comprising the steps of:

providing a fluid suspension of dispersed particles;

disposing a filter having a first side and a second side within said fluid suspension and flowing said fluid suspension across said filter from said first side to said second side such that a substantially known quantity of particles collect onto said first side of said filter;

removing said filter and said particles collected thereon from said fluid suspension; and passing a known volume of collection fluid sufficient to produce said fluid sample having said select concentration of particles through said filter, to remove substantially said particles collected on said first side, and to collect said particles within said known volume of collection fluid, to thereby produce said select concentration of particles.

2. A method according to claim 1 wherein said step of disposing a filter includes the step of providing a particle collection device having an intake port and an evacuation port and having said filter spanning said intake port.

3. A method according to claim 2 wherein said step of flowing said fluid includes the step of evacuating said particle collection device to draw fluid across said filter and through said intake port and into said collection device.

4. A method according to claim 1 wherein said step of passing a known quantity of collection fluid through said filter includes the step of applying a select fluid pressure within said collection device to force fluid collected therein back across said filter.

5. A method for collecting a fluid sample having a select concentration of particles, comprising the steps of:

providing a fluid suspension of dispersed particles:

disposing a filter having a first side and a second side within said fluid suspension and flowing said fluid suspension across said filter from said first side to said second side such that a substantially known quantity of particles collect onto said first side of said first filter;

removing said filter and said particles collected thereon from said fluid suspension; and passing a known volume of collection fluid through said filter, to remove substantially said particles collected on said first side, and to collect said particles within said known volume of collection fluid, wherein said step of passing a known volume of collection fluid through said filter comprises the steps of:

applying a select fluid pressure within said collection device to force fluid collected therein back across said filter; and disposing said filter collection device at a select angle and to generate thereby a drip of said collection fluid having said particles collected therein.

6. A method according to claim 1 comprising the further step of selecting a filter having a pore size adapted for collecting particles of a predetermined size.

7. A method according to claim 1 including the further step of lysing said collected particles.

8. A method according to claim 1 comprising the further step of providing a portion of said collected particles in said known volume of collection fluid as a sample for a diagnostic assay.

9. A method according to claim 1 wherein said step of flowing said fluid suspension includes the step of measuring a characteristic representative of the quantity of particles collected against said filter.

10. A method according to claim 9 including the further step of interrupting said step of flowing said fluid suspension responsive to a measured characteristic representative of a pre-selected quantity of particles.

11. A method according to claim 1 wherein said step of flowing said fluid suspension includes the further step of applying a known pressure to said fluid suspension.

12. A method according to claim 1 wherein said step of flowing said fluid suspension includes the further step of applying a succession of known pressures to said fluid suspension.

13. A method according to claim 11 wherein said step of flowing said fluid suspension includes the further step of measuring a characteristic representative of a rate of change of pressure.

14. A method according to claim 1 wherein said step of providing a fluid suspension of dispersed cells includes the step of providing said collected particles within said known volume of fluid, for incrementally increasing the concentration of said particles within said known volume of fluid.

15. A method according to claim 1 wherein said step of providing a fluid suspension of dispersed cells comprises the further steps of actuating a fluid having a sample material disposed therein.

* * * * *